United States Patent [19]
Armistead

[11] Patent Number: 5,638,420
[45] Date of Patent: Jun. 10, 1997

[54] STRADDLE INSPECTION SYSTEM

[75] Inventor: Robert A. Armistead, Los Altos Hills, Calif.

[73] Assignee: Advanced Research and Applications Corporation, Sunnyvale, Calif.

[21] Appl. No.: 674,919

[22] Filed: Jul. 3, 1996

[51] Int. Cl.⁶ .................................................. G01N 23/04
[52] U.S. Cl. ............... 378/57; 378/58; 378/146; 378/189; 378/198
[58] Field of Search ................................. 378/197, 198, 378/57, 58, 146, 189

[56] References Cited

U.S. PATENT DOCUMENTS

| | | | |
|---|---|---|---|
| 2,831,123 | 4/1958 | Daly | 378/198 |
| 3,766,387 | 10/1973 | Heffan et al. | 378/58 |
| 4,366,382 | 12/1982 | Kotowski | 378/57 |
| 4,430,568 | 2/1984 | Yoshida et al. | 250/358.1 |
| 4,599,740 | 7/1986 | Cable | 378/57 |
| 5,237,598 | 8/1993 | Albert | 378/99 |

*Primary Examiner*—Craig E. Church
*Attorney, Agent, or Firm*—Thomas Schneck

[57] ABSTRACT

A radiographic inspection apparatus for large containers, vehicles and structures having a movable frame which can straddle the container or object being inspected. The straddling frame has opposed parallel sides which carry a source of penetrating radiation and a detector array. The source or sources and detectors are moved along the length of a container while radiographic image data is being sequentially recorded. By summing or collecting the sequence of data over the length of a container as the straddling frame moves along, a full two-dimensional radiographic image of the container may be obtained. Radiographic images may be enhanced either by providing uniform motion for the straddling frame or by measuring non-uniform motion and compensating corresponding regions of the radiographic image.

48 Claims, 4 Drawing Sheets

STRADDLE INSPECTION SYSTEM

TECHNICAL FIELD

The invention relates to X-ray inspection systems for large objects such as cargo containers, and particularly for international shipping containers.

BACKGROUND OF THE INVENTION

There is an increasing interest in being able to noninvasively inspect the contents of such large objects as automobiles, trucks, rail cars and the international shipping containers used at seaports and airports. The objectives of such inspections are varied and include the detection of contraband at ports of entry; the detection of explosives at entrances to buildings or within baggage and containers; and, for commercial reasons, such as verifying the accuracy of customs declarations and shipping manifests.

This invention, in particular, addresses the growing problem of stolen cars being shipped to other countries for resale. The National Insurance Crime Bureau estimates that of the 1.5 million vehicles stolen annually in the U.S.A., 200,000 are shipped overseas. This costs insurance companies and consumers $1 billion to $4 billion annually. A principal method for exporting these stolen vehicles is to conceal them within the large, international, ocean-going shipping containers which are up to 44-ft long. Since one container can contain four automobiles and some ships can hold approximately 4,000 containers, the potential for loss is large and the problem of detection is considerable. Containers are loaded and closed at their departure point. The physical inspection of a high percentage of containers by U.S. Customs personnel is not a practical solution. It has been estimated that 15 person hours are required to unload and inspect a container. In addition to the direct cost of physical inspection, the delivery of the container is correspondingly delayed and such inspections break the shipper's trust and invalidates the carrier's insurance, opening up the possibility of claims for loss and damage.

An example is provided by the Port of Miami. Nearly 10,000 cargo vessels dock at Miami every year, unloading 35 million tons of freight. Tonnage at the port is growing at an annual rate of 10 percent. Currently, U.S. Customs can physically inspect less than 3 percent of the 200,000 ocean-going containers that enter Miami every year. Moreover, the Customs inspectors emphasize incoming cargo and a somewhat smaller fraction of exiting cargo is inspected. The Miami airport handles most of the U.S. air traffic for Central and South America with very large numbers of air cargo containers. While these containers are too small to conceal cars, other contraband is sometimes present, particularly upon import to the U.S.

Noninvasive inspections using X-ray beams to image the contents of containers as well as vehicles and rail cars are considered to be one of the most practical approaches to contraband detection and manifest verification. Many nations are implementing some form of X-ray imaging. In the U.S., a prototype system by Analytical Systems Engineering Corp. for inspecting containers was evaluated at the Port of Tacoma. U.S. Customs is employing X-ray inspection systems manufactured by American Science and Engineering at the U.S.-Mexican border to search for contraband in cars and trucks. In Europe, X-ray systems by Europscan of France have been installed at either end of the Eurotunnel (Channel Tunnel) to detect explosives in vehicles. Two X-ray systems (one Heimann; one British Aerospace) have been installed at the Hong Kong-China border for verifying the contents of trucks and truck-borne shipping containers. Large X-ray systems were also installed at the Port of LaHavre, France (Europscan) and the Port of Hamburg, Germany (Heimann).

There have been several patents issued that cover variations of the fixed-site inspection approach. For example, U.S. Pat. No. 4,366,382 to Kotowski discloses a fixed-site baggage inspection system that uses a conveyor belt to pass baggage between an X-ray beam and a line array of detectors.

Likewise, U.S. Pat. No. 4,430,568 to Yoshida presents an X-ray system for the inspection of packages, including large shipping containers. Here again, the system is installed in a fixed site and employs a conveyor to move the package or container between the X-ray source and detector array.

U.S. Pat. No. 4,599,740 to Cable discloses another variation of the fixed-site inspection approach, particularly addressing the inspection of large items such as international shipping containers. Although the system of this patent again is in a fixed site and uses a conveyor to move the container between the X-ray source and the detectors, the invention relates to the use of a "folded" sensor screen or device that requires less height than previous straight detector arrays.

U.S. Pat. No. 5,237,598 to Albert discloses a mobile system for large objects such as aircraft, boat hulls or lengthy pipelines. This invention instead of using a small X-ray spot and a large detector array for imaging large objects, employs a large area source and a single X-ray detector, or plurality of individual detectors spaced over the objects, which has a small X-ray sensitive area. Using this "reverse geometry" approach, an image is obtained of an area of the object approximately equal to the area of the source. By moving the source to the location of another detector, or by moving the object relative to the source, other areas of the object can be inspected in sequence. The principal advantage cited for this approach is that precise alignment is not required between the source and the detector, therefore, the source and detector do not have to be secured with respect to one another.

Except for the Albert patent, these systems have an objective related to that of the present invention—the noninvasive X-ray inspection of large objects, such as vehicles and international shipping containers. However, they all are different from the present invention in several fundamental ways. All of the systems installed to date are of the "car wash" type, i.e., they are permanently installed in large shielded structures, thus requiring that the object to be inspected (container, truck, car, etc.) be brought to the facility. Once at the facility, some form of conveyance is employed to transport the container or vehicle through the stationary X-ray source and detectors. Then, the conveyance must be returned to the starting point to pick up another container or car. This is a time consuming operation. The "car wash" inspection facility has a number of problems that will limit its use, especially at ports which are typically spread out over many areas, congested, and with a large number of separate terminals. As an example, the prototype X-ray inspection facility evaluated at the Port of Tacoma had to be located a few miles from the docks, was in a 6-acre site and employed an X-ray examination building that was 242 feet long. Furthermore, the inspection system had a reported throughput capability of only four to six vehicles or containers per hour. Thus, it is obvious that cost and logistics issues prevent the use of fixed-site X-ray inspection facilities at most, if not all, ports. The patent to Albert, on the other hand, deals with a mobile system in which the large area X-ray source required is limited to low energies. Thus, this system is primarily useful for thin walls of aircraft or ship hulls, not for highly attenuating vehicles or cargo containers.

SUMMARY OF INVENTION

An object of the present invention is to provide a radioscopic inspection system for the inspection of large shipping containers and, possibly, vehicles and rail cars principally to detect such contraband as stolen cars and drugs, but possibly also for verifying that manifests are accurate.

The present invention provides a radiographic inspection system that is mobile; is self scanning in that it moves the source and detectors past the object being inspected; and, images the contents of a container or vehicle without touching or moving it. Consequently, it is not encumbered by the problems and limitations of the fixed-site systems. It does not require any dedicated space and does not require movement of the containers or vehicles to a fixed inspection site. The present invention does not require any transport apparatus to move the object through the X-ray beam. Moreover, for rows of containers, the inspection rate is projected to be ten times that of the car wash type systems. Furthermore, for port facilities, the self-contained system can move under its own power to various port areas implying that one (or a few) systems can satisfy the inspection needs of a large port. Also, the system can use any of a number of commercial "point" X-ray sources selected on the basis of the energy and intensity required for the application.

The present invention features a self-propelled, wheeled vehicle "straddling" (passing over the object with one set of wheels on each side) the object to be inspected (international container, vehicle, rail car or other large object). A penetrating radiation source, such as an X-ray source, is mounted on one side of the vehicle and a linear detector array on the other side so that the X-ray beam passes through the object being inspected as the vehicle straddles it and moves past it. The electrical signals generated in the detectors due to the impinging X rays are transmitted to an "imaging computer", associated with the detector array, where the digital signals are processed and displayed on a workstation or some other display screen or recorder. The straddling of a container, combined with vehicle motion, sweeps a collimated X-ray beam along the length of the container. In this way the vertical column of image data produced at each increment of time is summed over time to produce a complete radiographic image. Images can be evaluated in real-time by an operator/analyst; can be printed or photographed to provide hard-copy evidence; or can be recorded for data transmission or later evaluation, and for archival purposes. A telemetry system could also be used for transmission of the inspection data to a control center.

BEST MODE FOR CARRYING OUT THE INVENTION

Figure 1:
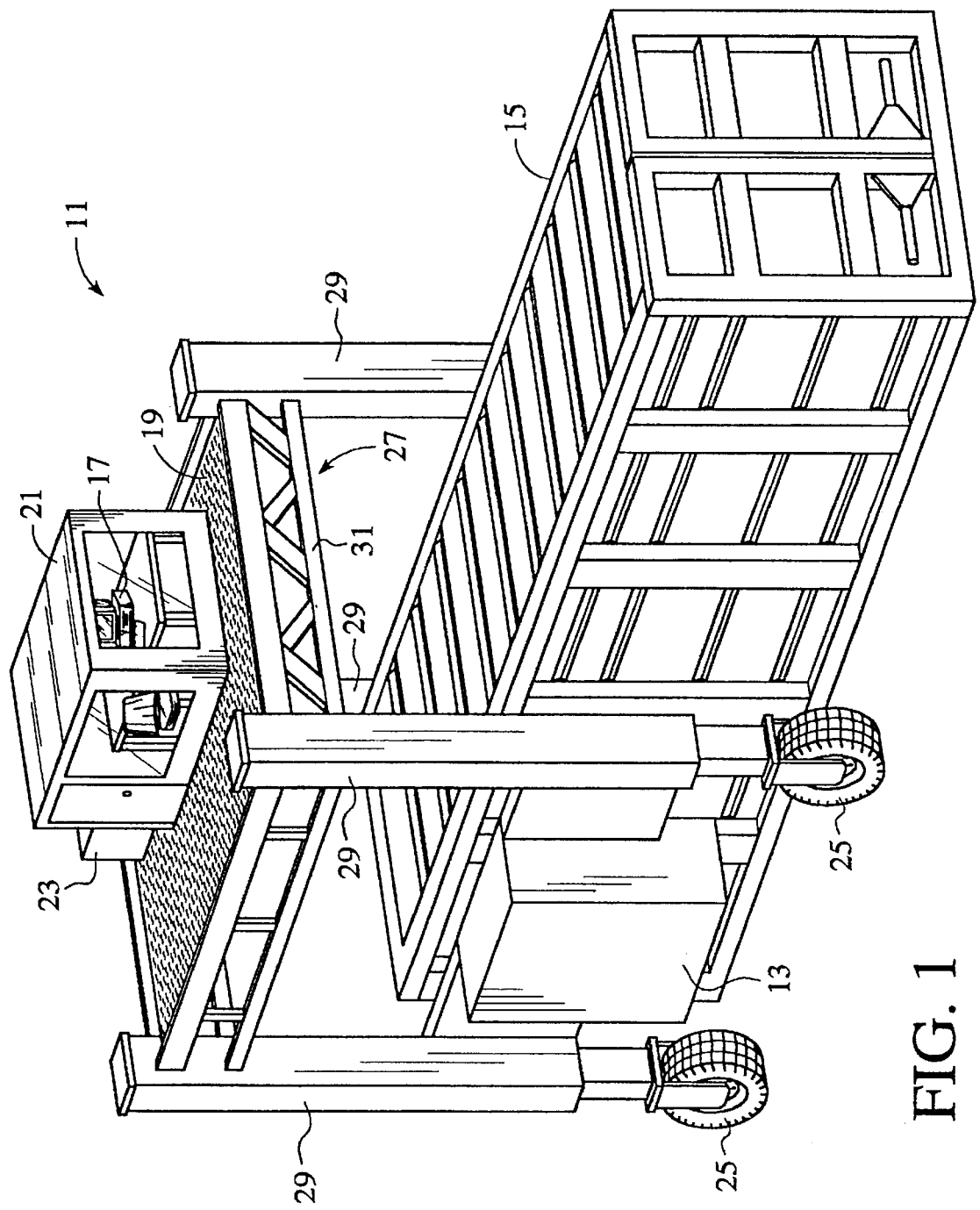
FIG. 1 is a perspective view of a straddle inspection vehicle astride a shipping container in accord with the present invention.
Figure 2:
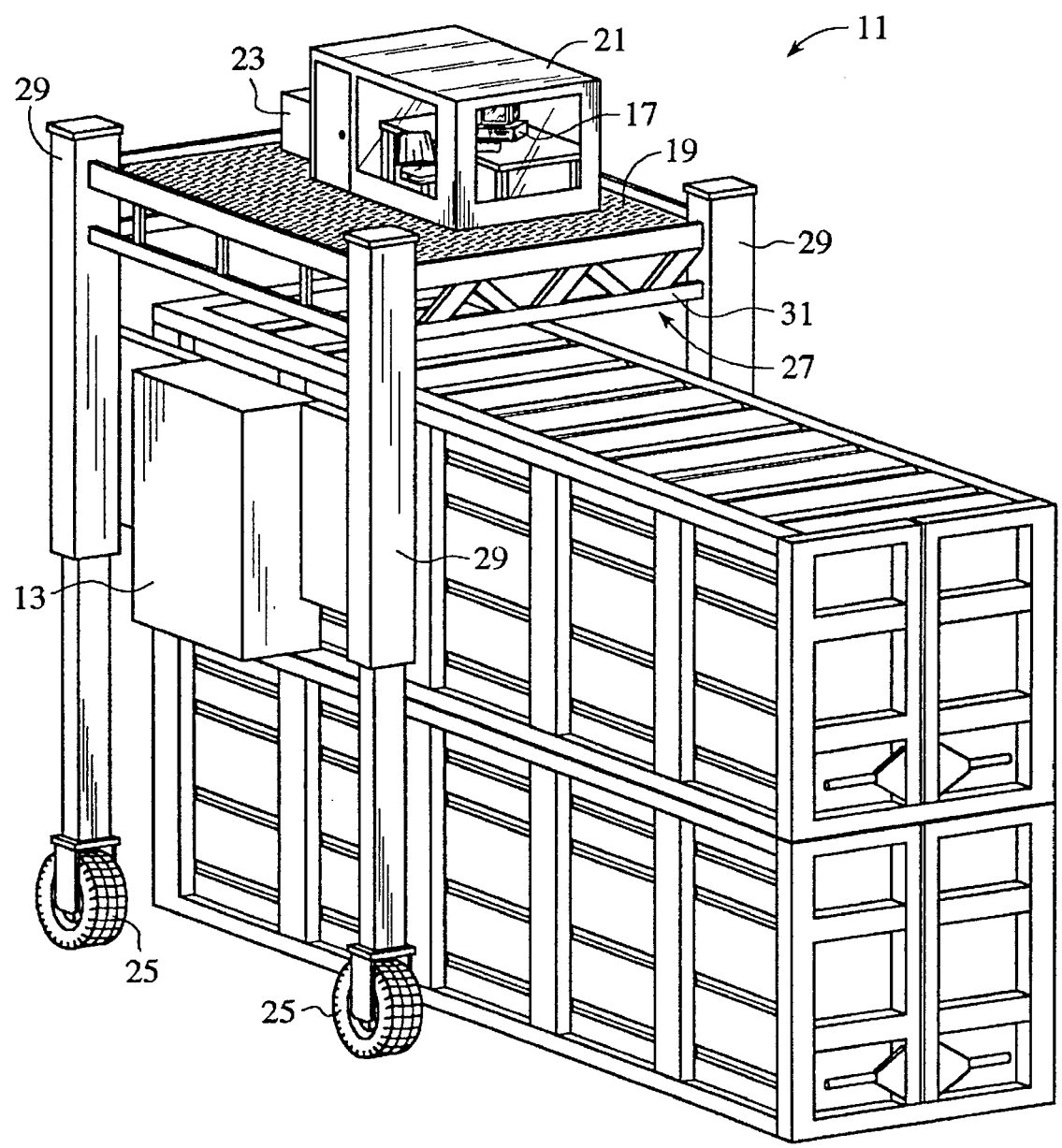
FIG. 2 is a perspective view of a straddle inspection vehicle, with extended legs, astride two shipping containers, in accord with the present invention.

With reference to FIGS. 1 and 2, the straddle carrier vehicle 11 serves as the support structure for an X-ray source 13; a detector array, not seen on the opposite side of container 15; the associated computer and image display system 17; shielding platform 19 for supporting and protecting the operator/analyst and for general operational safety; the operator/analyst room 21; and for associated power supplies, air conditioning equipment, power generating equipment, and radiation sensors, all contained in housing 23. The straddle carrier vehicle 11 has an engine under shielding platform 19, not seen, to enable movement under its own power to other locations within an inspection area or to other inspection areas. The vehicle's movement also provides the relative motion between the source 13 and detectors (held fixed with respect to each other) on the one hand and the container 15 or vehicle being inspected on the other hand, enabling an image to be formed of the object being inspected as the straddle vehicle passes over the object, thereby continuously illuminating the object by a beam of X rays which is collimated for sharpness.

The straddle carrier vehicle 11 may be of the type currently used at seaports to move ocean-going shipping containers. Manufacturers of such straddle carriers include Shuttlelift, Noell and others. The main difference between the straddle carrier vehicle 11 of this invention and the commercial units of the prior art is that there will not be a container "spreader" or "hoist" in the present invention. Instead, a radiation source housing 13 and a detector mounting housing are disposed across opposed legs 29. Platform 19 with supporting shielding, the operator/analyst cab 21, and the previously mentioned ancillary equipment are added to the top of the vehicle.

The straddle carrier vehicle is seen to have four wheels 25; a heavy-duty, rigid structural steel, inverted U-shaped frame 27; travel warning alarms; an industrial engine, either gasoline or diesel; and all controls required for operation. The inverted U-shaped frame 27 may have telescoping legs 29 and cross beams 31, as in FIG. 2. If employed, the telescoping legs 29 extend so that the straddle carrier is able to straddle two stacked containers with radiation source 13 sufficiently high to direct a beam to traverse the space through a container to detectors at the other side. The U-shaped frame 27 is U-shaped both in the longitudinal direction as well as in the crosswise direction. The cross beam 31 and similar peripheral beams supporting radiation shielding platform 19 should be braced to carry additional shielding where intense sources are used. Such intense sources may be linear accelerators producing electron beams which bombard a target, usually a metal film, emitting X rays. More than one source may be used. In particular, for some vehicles/containers a plurality of low-energy tube-type X-ray sources, or isotope sources which emit gamma-rays produce sufficient radiation to be measured at a plurality of detectors on the opposite side of the space between the legs. The choice of source type and its intensity and energy depends upon the sensitivity of the detectors, the radiographic density of the cargo in the space between the source and detectors; radiation safety considerations; and operational requirements, such as the inspection speed.

An alternative control system may be employed, particularly if the radiation safety of the operator/analyst or the weight of the shielding, etc. become issues. A remote operational feature is presently available on commercial straddle carriers permitting full operation of the vehicle from up to 200 yards away, with radio or cable transmission of control signals. This may eliminate the cab 21, display, and some of the controls from the straddle carrier, reducing the shielding and power consumption. In this case, the image data could be recorded digitally or transmitted for analysis at a different location.

In scanning a container, a new inspection method is used. A straddle carrier moves relative to a fixed container making one or more passes back and forth over the length of the container. The source and detector array are moved along the length of the container, continually recording the radiographic transmission image as the collimated radiation beam is swept along the container. For the detection of cars in a container, the source and detector position are fixed. However, for other inspection objectives, the height of the source and detector may need to be adjusted in elevation so that in one pass, a first elevation is scanned and then on another pass, a different elevation is scanned. In many instances, a single pass will be sufficient, but to verify data from a single pass, a second pass may be used.

Figure 3:
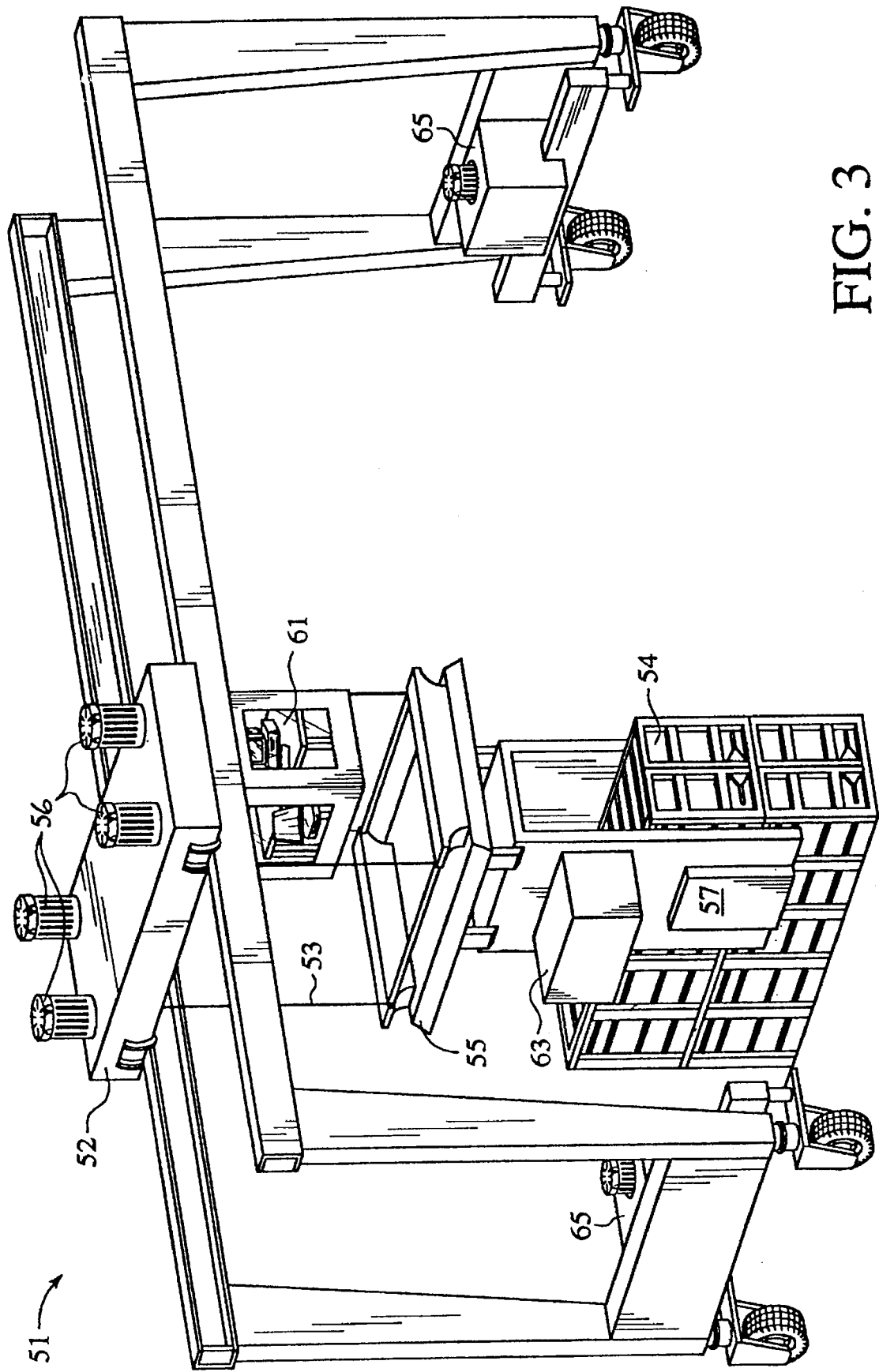
FIG. 3 is a perspective view of a straddle crane mounting an inspection system in accord with the present invention.

An alternative to the straddle vehicle would be any other type of movable conveyance that provides the requisite support for the source, detector array and ancillary apparatus; enables the source and detector to be held in alignment; and enables the source and detector to be passed at a uniform speed simultaneously on opposite sides of the container or vehicle being inspected. In particular, a straddle crane 51, shown in FIG. 3, uses a robotic gripper 55 and a connecting cable system 53, supported from rail mounted carriage 52, to maintain the spaced apart alignment of the source 57 and detectors, not seen behind container 54. Cable system 53 is raised and lowered by motors 56 in response to commands from the operator/analyst room 61. Associated power supplies, air conditioning equipment and radiation sensors are mounted in housing 63. Wheel and steering power engines or motors are mounted in housings 65. There are cranes of this general type in common use at ports designated as "straddle cranes" or "straddle lifts". In some instances, it may be desirable to operate the straddle vehicle or crane along a fixed route using wheel guides or mounted on rails.

A way to enhance radiographic images made by a moving source and detector has been found. In one embodiment, the motion of the straddle vehicle as it passes over and alongside the object being inspected is made steady and with constant velocity. Any irregularities in the motion of the straddle vehicle will result in distortions in the image, and so in the first embodiment motion is made as regular, even and constant as feasible using known control systems. For the detection of large contraband, such as stolen cars hidden within international shipping containers, only coarse spatial resolution in the image is required, i.e. approximately one inch. In such cases, it may be sufficient to control the motion procedurally, i.e., by bringing the straddle vehicle to approximately a constant speed with a speed controller, i.e. "cruise control", prior to passing over the container or rail car being inspected and by maintaining that speed as accurately as possible using the straddle vehicle's throttle.

In a second embodiment, for applications such as the detection of drugs, hidden compartments, false walls, and the verification of manifests, higher resolution will be required. For this purpose, irregularities of motion are measured and the radiographic image is correspondingly corrected. To accomplish this, one or more motion encoders can be affixed to one wheel of the straddle vehicle. For example, an encoder measures the rotational velocity of the wheel and transmits a corresponding electrical signal to the imaging system's computer. Wheel encoders are sometimes known as shaft angle encoders. If there is a change in speed, the computer automatically includes a corresponding compensation in the timing of the detector signals for that location, thereby eliminating nonuniform-motion-induced image distortions. As an alternative to the wheel encoder, a linear strip bearing evenly spaced bars can be attached to the side of each container using magnetic attachment, tape or other suitable means. During the imaging procedure, the strip can be "read" by one of several commercially available detectors. The linear strip and detector form an optical encoder producing a signal from the reflected or scattered light that can be used to correct the image data for motion-induced irregularities. Vertical as well as horizontal motion can be measured. In addition to linear translation encoding, for some applications it may be desirable to encode other system motions, such as the pitch and yaw of the vehicle. Both embodiments are defined as a radiographic image enhancement means.

Due to the large size of the containers or cars and the possibility of cargo that highly attenuates the X-ray beam, the preferred source is a linear accelerator (linac) operating with an accelerating potential in the millions of volts (MV) range. Such linacs are commercially available with accelerating potentials over the range from 2 MV to 15 MV. The higher the energy of the source, the more X rays that are produced. Also, at higher energies, the mass attenuation coefficient of materials decreases, so that the X rays can penetrate a greater thickness of the material. Linac sources produce high-energy bremmstrahlung X rays in a series of low-duty-cycle pulses. This signal format conveniently lends itself to the use of electronic techniques which correct for drift in the detector dark current and for amplifier offsets and, with the use of a suitable reference detector, for variations in source output. These techniques improve the noise and linearity and, thus, the quality of the radiographic images. Alternatives to a linac, would be a radioisotopic source or an X-ray tube. However, the intensity of the radiation from isotopes is several orders of magnitude lower than that from linacs and that from tubes is of lower intensity and less penetrating, in both cases generally limiting image quality and inspection speed.

The preferred detector arrangement consists of a linear array of solid-state detectors of the crystal-diode type. A typical arrangement uses cadmium tungstate scintillating crystals to absorb the X rays transmitted through the object being inspected and to convert the absorbed X rays into photons of visible light. There are alternative crystals such as bismuth germinate and sodium iodide. The crystals can be directly coupled to a suitable detector, such as a photodiode or photomultiplier; however, it is preferred to use optical light pipes to carry the light to the detectors along a path at a sharp angle to the X-ray beam so that the detectors can be shielded from the direct X rays and from most of the scattered X rays. The preferred detectors are a linear arrangement of photodiodes, which though unity-gain devices, provide advantages over photomultiplier detectors in terms of operating range, linearity and detector-to-detector matching. An area detector is an alternative to linear array detectors. Such an area detector could be a scintillating strip, such as cesium iodide or other, viewed by a suitable camera or optically coupled to a charge coupled device (CCD). When an area detector is used, light pipes map the light from the linear scintillator onto discrete areas of the area detector. In the computer, the signals from the area detector are remapped back to a linear column of data and stored in memory. As the beam and detectors move with the straddle vehicle, a two-dimensional image is formed by the concatenation of individual columns over the time necessary for the straddle vehicle to pass over the container or other object being inspected.

For high-resolution applications, the electronics used to read out the detector signals typically feature auto-zeroed, double-correlated sampling to achieve ultra-stable zero drift and low-offset-noise data acquisition. Automatic gain ranging may be used to accommodate the wide attenuation ranges that can be encountered with large containers and vehicles.

Figure 4:
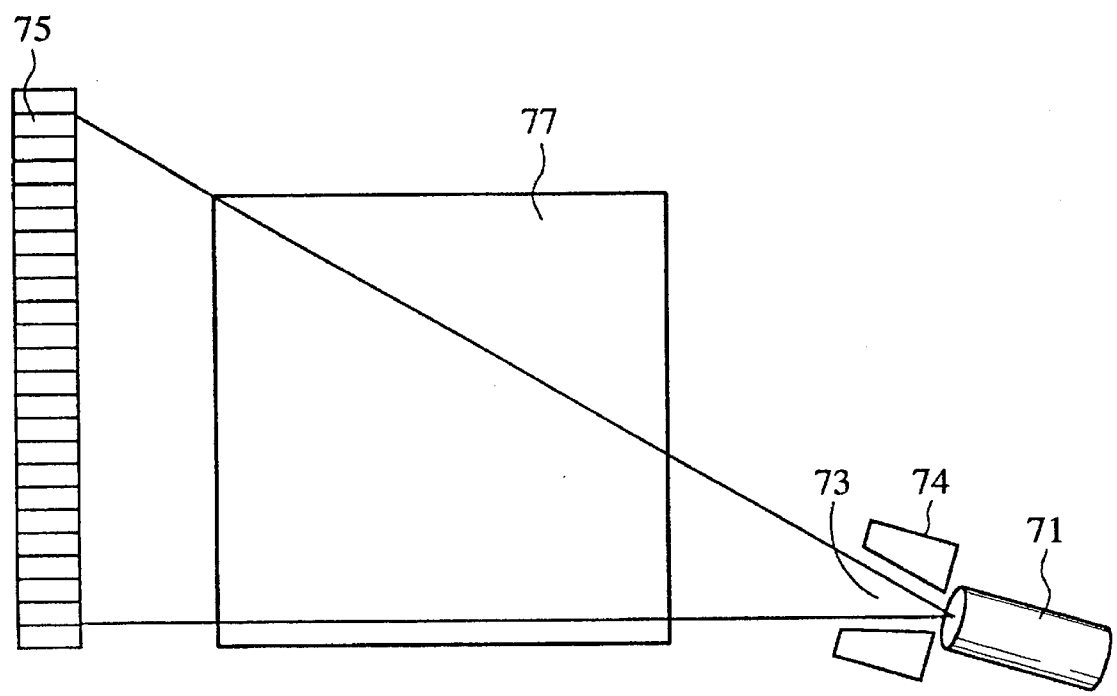
FIG. 4 is a side plan view of radiographic inspection of a container in accord with the present invention.

With reference to FIG. 4, an X-ray source 71 is used to produce X rays 73 which are collimated to a narrow beam with essentially parallel sides. A collimator 74 is designed to produce either a fan of X rays or a cone beam or a series of "pencil beams". Collimation serves to limit the X rays that are scattered from the object to be inspected 77 into the detectors 75, which reduces the contrast in the images. Collimation also reduces the shielding required for radiation protection.

The height of the detectors, which determines how much of the containers are inspected, is selected on the basis of the objective of the inspection. For example, if the objective is to detect cars hidden within an international shipping container 77, the characteristic signatures identifying the presence of the car could be the large metal components such as the engine block, transmission and axles. In such a case, the inspection height at the center of the container may be limited to four or five feet from the floor level. Other areas of interest may be the detection of hidden compartments under the floor, in the ceiling and behind false walls at the end of the container. In FIG. 4, the detector array is approximately equal to the container height, in this case, eight feet. This configuration enables coverage from just above ground level to six feet (6 ft.) at the container center as well as examining areas of the back and side walls.

In addition to the use of detectors opposite from the source and in direct line with it to measure the transmitted X rays, a detector array can, in addition, be employed on the source side of the straddle vehicle. These detectors would be aligned to detect a portion of the Compton scattered, i.e. "backscattered", X rays. Likewise, another detector array can also be employed on the detector side of the vehicle, but out of the transmitted X-ray beam, to detect the forward scattered X rays. Such scattered X rays have proven efficacious in detecting the presence of low-atomic-number contraband such as drugs and explosives hidden within the walls of containers, trucks, etc.

With the geometry shown in FIG. 4, a portion of the container or large vehicle would not be imaged. Although not necessary to detect stolen cars, drugs submerged in tanker cars, etc., the full inspection of containers and cars may be desired for other applications, such as the verifications of manifests. For such requirements, alternative configurations could be used. For example, as discussed previously, the availability of straddle carriers with telescoping legs allows the source and detector array to be mounted so that they could be moved to different elevations. Also, the source could be mounted near the midplane on a tilt apparatus which would direct the X rays upwards or downwards and a taller detector array, or one that could be moved to different heights, could be used.

I claim:

1. An apparatus for radiographic inspection of vehicles and large containers comprising,
   a movable, inverted U-shaped frame having first and second parallel vertical sides spaced apart by a distance greater than a container to be inspected,
   means for moving the frame relative to a container to be inspected,
   a penetrating radiation source disposed on a first side of the frame having a beam directed toward the second side,
   a detector disposed to record radiation traversing the space between the sides, producing a radiographic signal indicative of material in the space, and
   means for summing radiographic signals along a dimension of the container thereby forming a radiographic image of the contents of the container.

2. The apparatus of claim 1 wherein the inverted U-shaped frame is the frame of a straddle carrier vehicle having two pairs of spaced apart wheels, one pair of wheels associated with each of the sides.

3. The apparatus of claim 2 wherein the means for moving the frame relative to a container comprises an engine mounted on the frame.

4. The apparatus of claim 3 wherein said means for moving the frame further includes a remote control means for guiding said frame.

5. The apparatus of claim 3 wherein said means for moving the frame includes control means for guiding said frame at constant velocity.

6. The apparatus of claim 1 wherein the inverted U-shaped frame comprises a straddle crane.

7. The apparatus of claim 1 wherein the radiation source comprises a linear accelerator.

8. The apparatus of claim 1 wherein the radiation source comprises an X-ray tube.

9. The apparatus of claim 1 wherein the radiation source comprises an isotope.

10. The apparatus of claim 1 further comprising a plurality of penetrating radiation sources having beams traversing said space and a plurality of detectors disposed to intercept said beams after traversing said space.

11. The apparatus of claim 1 wherein the detector comprises a linear array of detectors.

12. The apparatus of claim 1 wherein the detector comprises an area array of detectors.

13. The apparatus of claim 1 wherein the detector comprises fluorescent material emitting visible light in response to penetrating beam impingement and an optical detector disposed to receive light from the fluorescent material.

14. The apparatus of claim 13 wherein said optical detector comprises a photodiode detector.

15. The apparatus of claim 13 wherein said optical detector comprises a photomultiplier detector.

16. The apparatus of claim 13 wherein said optical detector comprises an area detector.

17. The apparatus of claim 16 wherein said area detector is a video camera.

18. The apparatus of claim 16 wherein said area detector is a charge coupled device (CCD) array.

19. The apparatus of claim 16 wherein said area detector is a photodiode array.

20. The apparatus of claim 16 wherein said area detector is a photomultiplier array.

21. The apparatus of claim 16 wherein light pipes couple the area detector to said strip of fluorescent material.

22. The apparatus of claim 1 further comprising a beam collimator means for producing a fan-shaped beam.

23. The apparatus of claim 1 further comprising a beam collimator means for producing a plurality of pencil beams.

24. The apparatus of claim 1 further comprising a beam collimator means for producing a cone beam of X rays.

25. The apparatus of claim 1 further comprising a radiographic image enhancement means operatively associated with the means for summing radiographic signals.

26. The apparatus of claim 25 wherein the radiographic image enhancement means comprises a speed controller for the means for moving the frame.

27. The apparatus of claim 25 wherein the radiographic image enhancement means comprises motion encoders.

28. The apparatus of claim 27 wherein said motion encoders are wheel encoders.

29. The apparatus of claim 27 wherein said motion encoders are linear strip optical encoders.

30. An apparatus for the radiographic inspection of large containers comprising, a straddle carrier vehicle or crane having two sets of wheels supported by a frame, the wheels mutually spaced apart on opposite sides of the frame by a distance exceeding the width of a container to be inspected such that one set of wheels is on each side of the container in a straddle relation therewith, the vehicle having propulsion means for moving relative to the container, an X-ray source disposed on a first side of said straddle carrier vehicle having a beam directed toward the second side, an X-ray detector array disposed to intercept the X-ray beam upon traversing the space between mutually spaced apart sets of wheels and to produce a signal representing the X-ray image through the container, and means for displaying or recording the image signal.

31. The apparatus of claim 30 wherein said straddle carrier vehicle has extendable legs.

32. The apparatus of claim 30 wherein said propulsion means has remote control means for guiding the straddle carrier.

33. The apparatus of claim 30 having means for raising and lowering the source and the detector.

34. The apparatus of claim 30 further comprising a radiographic image enhancement means operatively associated with the means for displaying or recording the image signal.

35. The apparatus of claim 34 wherein the radiographic image enhancement means comprises a speed controller associated with said propulsion means.

36. The apparatus of claim 34 wherein the radiographic image enhancement means comprises motion encoders.

37. The apparatus of claim 36 wherein said motion encoders are wheel encoders.

38. The apparatus of claim 36 wherein said motion encoders are linear strip optical encoders.

39. The apparatus of claim 30 having a plurality of X-ray sources disposed on a first side of said straddle carrier having beams directed toward the second side and a plurality of X-ray detectors disposed to intercept the X-ray beams upon traversing said space.

40. A method of radiographic inspection of large opaque objects, such as cargo containers, rail cars, trucks and the like comprising, establishing a stationary position for a large opaque object having a length, height and width, straddling the width of the large object with a frame having opposed sides, directing a beam of penetrating radiation through the object from one side of the frame to the opposite side, detecting the beam passing through the object and producing a visible radiographic signal for a single location corresponding to the detected beam, moving the frame and beam along the length of the object, summing the radiographic signals for a plurality of frame and beam positions along the length of the object thereby forming a two-dimensional radiographic image of the object.

41. The method of claim 40 wherein said beam is a fan shaped beam.

42. The method of claim 40 further defined by moving the frame and beam at different elevations of the cargo container.

43. The method of claim 40 further defined by straddling the object with a straddle vehicle.

44. The method of claim 40 further defined by straddling the object with a straddle crane.

45. The method of claim 40 further defined by enhancing radiographic images by moving the frame and beam along the length of the object with uniform motion.

46. The method of claim 40 further defined by enhancing a radiographic image by measuring and compensating any non-uniform motion of the frame and beam along the length of the object.

47. The method of claim 46 wherein said measuring is by monitoring wheel motion with a wheel encoder.

48. The method of claim 46 wherein said measuring is by monitoring an optical encoder.

* * * * *